United States Patent
Yik et al.

(10) Patent No.: US 10,332,482 B2
(45) Date of Patent: Jun. 25, 2019

(54) AUTOMATED DISPLAY DIMNESS CONTROL FOR A MEDICAL DEVICE

(71) Applicant: Fresenius Medical Care Holdings, Inc., Waltham, MA (US)

(72) Inventors: Kelly Yik, Hayward, CA (US); Matthew Doyle, Concord, CA (US); Aiyuan Wang, San Ramon, CA (US); Thomas Merics, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/866,166

(22) Filed: Sep. 25, 2015

(65) Prior Publication Data
US 2017/0092227 A1    Mar. 30, 2017

(51) Int. Cl.
*G09G 5/10* (2006.01)
*G16H 40/63* (2018.01)
*A61M 1/14* (2006.01)
*G06F 19/00* (2018.01)

(52) U.S. Cl.
CPC .............. *G09G 5/10* (2013.01); *G16H 40/63* (2018.01); *A61M 1/14* (2013.01);
(Continued)

(58) Field of Classification Search
None
See application file for complete search history.

(56) References Cited

U.S. PATENT DOCUMENTS 8,870,812 B2    10/2014  Alberti et al.
2003/0212314 A1*  11/2003  Takahashi ............... A61M 1/16
                                                            600/310
(Continued)

FOREIGN PATENT DOCUMENTS

EP       2335753 A1      6/2011
WO    WO199957601 A1    11/1999
WO    WO2015124569 A1    8/2015

OTHER PUBLICATIONS

Notification of Transmittal of the International Search Report and the Written Opinion of the International Searching Authority for corresponding PCT Application No. PCT/US2016/053076, dated Dec. 14, 2016, 15 pages.

*Primary Examiner* — Lunyi Lao
*Assistant Examiner* — Benjamin X Casarez
(74) *Attorney, Agent, or Firm* — Fish & Richardson P.C.

(57) ABSTRACT

A medical device, such as a peritoneal dialysis machine, includes a sensor for sensing motion and/or user proximity in the vicinity of the medical device for the purpose of automated dimming a display of the medical device. In the event of a lack of user-activity on a machine interface and a lack of movement detected by the proximity sensor, the machine display is automatically dimmed to minimize power-consumption and provide an enhanced medical device for night therapies in a home or clinic environment. The machine display may be dimmed in the event of an alarm-free machine condition, where no machine activity is detected and/or where no movement is detected by the sensor over one or more time periods. When machine activity is detected, when movement is detected by the proximity sensor, and/or in the event of a machine alarm or warning, the machine display may be automatically undimmed.

24 Claims, 5 Drawing Sheets

(52) U.S. Cl.
CPC . *A61M 2205/502* (2013.01); *A61M 2205/583* (2013.01); *G06F 19/3481* (2013.01); *G09G 2320/0626* (2013.01); *G09G 2354/00* (2013.01); *G09G 2380/08* (2013.01)

(56) References Cited

U.S. PATENT DOCUMENTS

| | | | |
|---|---|---|---|
| 2005/0235993 A1 | 10/2005 | Baecke et al. | |
| 2006/0229557 A1* | 10/2006 | Fathallah | G06F 19/3406 604/131 |
| 2008/0068519 A1* | 3/2008 | Adler | G06F 1/1626 348/838 |
| 2009/0131757 A1* | 5/2009 | Jayaram | A61B 5/0205 600/300 |
| 2009/0157432 A1* | 6/2009 | Palmroos | A61M 5/142 705/3 |
| 2010/0295839 A1* | 11/2010 | Nagaya | G06F 1/3265 345/212 |
| 2011/0105854 A1* | 5/2011 | Kiani | G06F 19/327 600/300 |
| 2012/0245447 A1* | 9/2012 | Karan | A61B 5/14532 600/365 |
| 2012/0293404 A1* | 11/2012 | Federico | G06F 3/0304 345/156 |
| 2012/0293481 A1* | 11/2012 | Chaji | G06F 3/038 345/212 |
| 2013/0165847 A1* | 6/2013 | Scarpaci | A61M 1/28 604/28 |
| 2014/0180595 A1* | 6/2014 | Brumback | A61B 5/0015 702/19 |
| 2014/0200426 A1* | 7/2014 | Taub | A61B 5/14532 600/347 |
| 2014/0230071 A1* | 8/2014 | Adam | G06F 21/60 726/26 |
| 2014/0266983 A1 | 9/2014 | Christensen | |
| 2014/0267003 A1 | 9/2014 | Wang et al. | |
| 2015/0014249 A1 | 1/2015 | Alberti et al. | |
| 2015/0025449 A1* | 1/2015 | Yuds | A61M 1/288 604/28 |
| 2015/0164390 A1* | 6/2015 | Larvenz | G06F 19/3406 600/365 |
| 2015/0253860 A1 | 9/2015 | Merics et al. | |
| 2017/0147166 A1* | 5/2017 | Schaefer | G06F 3/0482 |

* cited by examiner

AUTOMATED DISPLAY DIMNESS CONTROL FOR A MEDICAL DEVICE

TECHNICAL FIELD

This application relates generally to medical device displays.

BACKGROUND

Hemodialysis and peritoneal dialysis machines removes toxic substances and metabolic waste from the body. Hemodialysis is typically done multiple times a week in a clinic or home environment, whereas peritoneal dialysis is done several times a day and is typically done in a home environment. In particular, peritoneal dialysis is often performed overnight while a patient is asleep.

Hemodialysis and peritoneal dialysis machines typically have a monitor or display which conveys information related to treatment status, physiological patient parameters, machine parameters, alarm status, and the like. These displays may be bright, resultant of the need to be able to convey said information to a machine operator who may be standing several feet away from the machine, and as a result, these displays may consume a significant amount of power. In the case of peritoneal dialysis patients undergoing night-time therapies, these displays may also be a distraction for patients attempting to sleep during the therapy. Control of the dimming of machine displays is typically initiated by a manual interaction with the display by a user, such as for the 2008K@Home machine by Fresenius Medical Care.

Accordingly, it would be desirable to provide a system for automatically dimming the machine display, such as to reduce machine power consumption, reduce manual interaction with medical device displays, and/or enhance the efficacy of hemodialysis and/or peritoneal dialysis machines being used for night-time therapies.

SUMMARY

According to the system described herein, a medical device, such as a peritoneal dialysis machine and/or a hemodialysis machine, is equipped with an automated display dimming device for automatically dimming a display of the medical device without requiring a manual user action to dim the display. After the medical device is powered on, properly configured to initiate the intended therapy, and the intended therapy has been initiated—the dimming functionality may be active. It should be appreciated that the dimming feature may be advantageously used during a therapy mode; however, the dimming feature may additionally be used in machine modes such as rinse/disinfection, service mode and/or a no program state.

In an implementation, the automated display dimming feature of the system described herein may only be functional in an alarm-free condition. Once an alarm-free condition has been achieved, machine interaction may be monitored (e.g. pressing the touchpad, keypad, keyboard, the machine display in the case of a touch screen, or the like). In an implementation, the functionality of the automated display dimness feature may be activated or deactivated through a service mode setting. Alternatively, the automated display dimness feature may be a default feature. Additionally, the duration of machine interface inactivity before having the machine display enter a dimmed state may be adjustable through a service mode setting. Alternatively, the duration of machine interface inactivity before having the machine display enter a dimmed state may be a preset value.

According to the system described herein, a medical system includes a medical device having a display and includes a display dimness control device for controlling a dimness of the display. The display dimness control device includes at least one sensor that includes a motion sensor and/or a proximity sensor. A control unit is coupled to the medical device and the at least one sensor. The control unit automatically controls dimness of the display based on a state of the medical device and input received from the at least one sensor. The state of the medical device may include an alarm-free condition of the medical device and/or a condition of manual interaction with the medical device via a machine interface. The medical device may be a peritoneal dialysis machine or a hemodialysis machine.

In various implementations, the control unit may also control operations of the medical device. Further, the control unit may cause the display to automatically enter a dimmed state when the medical device is in an alarm-free condition for a first time period, when no activity occurs on a machine interface of the medical device for a second time period, and when no movement and/or no user proximity is detected in a vicinity of the medical device by the at least one sensor for a third time period. The first time period, the second time period, and the third time period may be independent of each other. The control unit may cause the display to automatically exit a dimmed state according to at least one of the following: (i) when an alarm occurs on the medical device, (ii) when user activity occurs on the machine interface, and/or (iii) when movement and/or user proximity is detected by the at least one sensor in the vicinity of the medical device. During a dimmed state of the display, the control unit may control presentation of a clock on the display, and the clock may be a therapy clock showing a duration of a therapy performed by the medical device. Additionally and/or alternatively, during a dimmed state of the display, the control unit may control presentation of treatment status information on the display.

According further to the system described herein, a method for automated dimness control of a medical device is provided. The method includes monitoring for movement in proximity of the medical device using at least one sensor, monitoring for an alarm on the medical device, and monitoring for activity on a machine interface of the medical device. The method further includes automatically causing a display of the medical device to enter a dimmed state when the medical device is in an alarm-free condition for a first time period, when no activity on the machine interface occurs for a second time period, and when no movement and/or no user proximity is detected in a vicinity of the medical device by at least one sensor for a third time period.

In various implementations, the method may further include causing the display to automatically exit the dimmed state according to at least one of the following: (i) when an alarm occurs on the medical device, (ii) when user activity occurs on the machine interface, and/or (iii) when movement and/or user proximity is detected by the at least one sensor in the vicinity of the medical device. The medical device may be a peritoneal dialysis machine or a hemodialysis machine. The first time period, the second time period, and the third time period may be independent of each other. During a dimmed state of the display, the control unit may control presentation of a clock on the display, and the clock may be a therapy clock showing a duration of a therapy performed by the medical device. Additionally and/or alternatively, during a dimmed state of the display, the control unit may control presentation of treatment status information on the display.

In various implementations, the dimness control unit, that may be part of and/or separate from the control unit of the medical device, includes at least one specific processor configured to control the entry and exit into the display dimmed state and that executes software stored on a non-transitory computer-readable medium that controls performance of one or more of the features described herein.

BRIEF DESCRIPTION OF THE DRAWINGS

Embodiments and features of the system described herein are explained with reference to the several figures of the drawings, which are briefly described as follows.

DETAILED DESCRIPTION OF VARIOUS EMBODIMENTS

Figure 1:
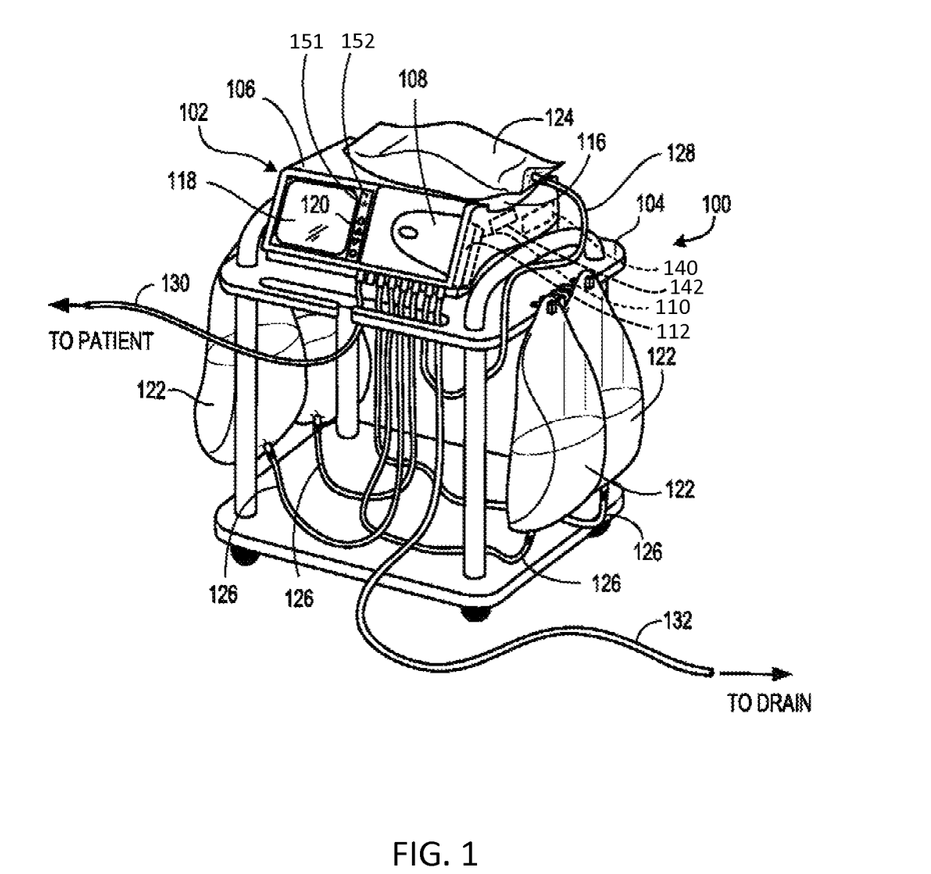
FIG. 1 is a schematic illustration showing an example of a peritoneal dialysis system having automated display dimness control features in accordance with an embodiment of the system described herein.

FIG. 1 shows a dialysis system having automated display dimness control features in accordance with an embodiment of the system described herein. The dialysis system may be a peritoneal dialysis ("PD") system 100 that includes a PD machine (also referred to as a PD cycler) 102 seated on a cart 104. Although a PD system is principally discussed herein, it is noted that the system described herein may be used in connection with other types of medical devices and/or dialysis systems, including, for example, hemodialysis systems. The PD machine 102 includes a housing 106, a door 108, and a cassette interface 110 that contacts a disposable PD cassette 112 when the cassette 112 is disposed within a cassette compartment formed between the cassette interface 110 and the closed door 108. A heater tray 116 is positioned on top of the housing 106. The heater tray 116 is sized and shaped to accommodate a bag of dialysate (e.g. a 5 liter bag of dialysate). The PD machine 102 also includes a user interface such as a touch screen display 118 and additional control buttons 120 that can be operated by a user (e.g. a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The drain line 132 can be connected to a drain or drain receptacle and can be used to pass dialysate from the cassette 112 to the drain or drain receptacle during use.

The PD machine 102 includes a control unit 140 (e.g. a processor) and one or more sensors, such as a proximity sensor 151 and/or a motion sensor 152, that may detect the presence and/or motion of a nearby user. The control unit 140 can receive signals from and transmit signals to the touch screen display 118, the control panel 120, the proximity sensor 151, the motion sensor 152, and the various other components of the PD system 100. The control unit 140 includes automated dimness control features that control the dimness/brightness of the display 118 based on inputs received from the proximity sensor 151 and/or the motion sensor 152. It is noted that although a proximity sensor and motion sensor are discussed herein, other types of sensors that detect the presence, motion and/or other attributes of a nearby user may be used in connection with the system described herein.

The PD machine 102 may also include a data storage and/or transmission component 142 that may be coupled to the control unit 140 and that may enable the storage of data on the PD machine and/or the transmission of data to and from the PD machine 102. In various implementations, the data may include prescription information, treatment data and/or other therapy-based data and/or may include authorization information and/or other user profile-based information. In various implementations, the component 142 may include a wired connection to a network/Internet, an interface for receiving a physical storage unit, such as a universal serial bus (USB) memory unit, that may be used to transfer and receive data and/or wireless transmission components for transmitting or receiving data and/or other signals wirelessly. The wireless transmission components may include components for short range wireless transmission technologies, such as Bluetooth and/or near field communications (NFC technologies), for communication with one or more peripheral devices and/or network transmission components for transmitting and receiving data and/or other signals wirelessly via a telecommunications network and/or the Internet with one or more remote servers. In connection with transmission, data may be secured and/or encrypted via the control unit 140 using appropriate security and encryption protocols according to applicable laws and regulations governing transmission of sensitive data and/or protected medical information.

In an embodiment, the automated display dimming feature of the system described herein may only be functional in an alarm-free condition. Once an alarm-free condition has been achieved, machine interaction may be monitored (e.g. pressing the touchpad, keypad, keyboard, the machine display in the case of a touch screen, or the like). In an embodiment, the functionality of the automated display dimness feature may be activated or deactivated through a service mode setting. Alternatively, the automated display dimness feature may be a default feature. Additionally, the duration of machine interface inactivity before having the machine display enter a dimmed state may be adjustable through a service mode setting (e.g. 10 seconds to 5 minutes). Alternatively, the duration of machine interface inactivity before having the machine display enter a dimmed state may be a preset value (e.g. 5 minutes).

Once a period of machine interface inactivity surpasses either the preset value or the value set in service mode, and if the machine is in an alarm-free condition, the machine display automatically enters a dimmed state. If the machine is not in an alarm-free condition and the period of machine interface inactivity surpasses either the preset value or the value set in service mode, the machine display would not enter a dimmed state until an alarm-free condition was established. Determining that an alarm-free condition has been established may include determining that no alarms on the medical device have occurred over a suitable time period. If obtaining an alarm-free condition requires interaction with the machine interface, the period of machine interface inactivity would be reset and the machine display would enter a dimmed state once the machine interface inactivity again surpassed the preset value or value set in service mode.

In an embodiment, the machine display in a dimmed state may display the clock time. Additionally and/or alternatively, the machine display in a dimmed state may display the clock time and the machine treatment clock to convey the duration of the therapy. In another embodiment, the machine display in a dimmed state may display the treatment clock in addition to a background screensaver to convey the fact the machine was turned on. The screen saver may be either a preset screen saver or, alternatively, a screen saver selected from a group of available screen savers selectable in service mode. In yet another alternative embodiment, the machine display in a dimmed state would display the clock time and the machine status bar to convey machine state and information messages not considered to be alarms or warnings (e.g. Online Clearance Tests, Filling Programs, and Online Pressure Holding Tests for a Hemodialysis machine). One of the above-noted embodiments for the displayed information on the machine display in a dimmed state may be a preset option, or alternatively, a service mode setting may be provided that allows for the selection of one of these four embodiments of the machine display in a dimmed state. It should be appreciated that if desired, a combination of these embodiments for the machine display in a dimmed state may be either a preset option or selectable option in service mode.

When the machine display is in a dimmed state the machine may monitor machine alarm and warning state and/or the machine interface. In the event of either machine interface interaction or the occurrence of a machine alarm or warning, the machine display may be immediately undimmed. Once the alarm or warning is addressed, or once interaction with the machine interface is no longer detected, the machine would again dim the machine display once the machine interface inactivity surpassed either the preset value or the value set in service mode.

In an embodiment, the machine may be equipped with a proximity sensor for detecting movement in the nearby proximity of the machine (e.g. within 10 feet of the front of the device). In this embodiment, the machine display may require the following conditions to enter a dimmed state: a) an alarm-free condition, b) a period of machine interface inactivity that surpasses either the preset value or the value set in service mode, and/or c) where a lack of movement is detected by the proximity sensor in the nearby proximity of the machine. When these three conditions were met, the machine display would be capable of entering a dimmed state as described herein.

In the event of machine interface interaction, the occurrence of a machine alarm or warning, or the detection of movement by the proximity sensor, the machine display would be immediately undimmed. Once the alarm or warning is addressed, once interaction with the machine interface is no longer detected, or once movement by the proximity sensor is no longer detected, the machine would again dim the machine display once time periods over which the above conditions are monitored have surpassed either the preset values or the values set in service mode for suitable time periods for determining an action based on these conditions. For example, it should be appreciated that depending on the sensitivity of the proximity sensor it may be desirable to include an added delay before dimming the machine display after no longer detecting machine movement. The delay may either be a preset value or an adjustable value set in service mode. In this way, the machine display could exit and re-enter a dimmed state without the need for machine interface interaction.

Figure 2:
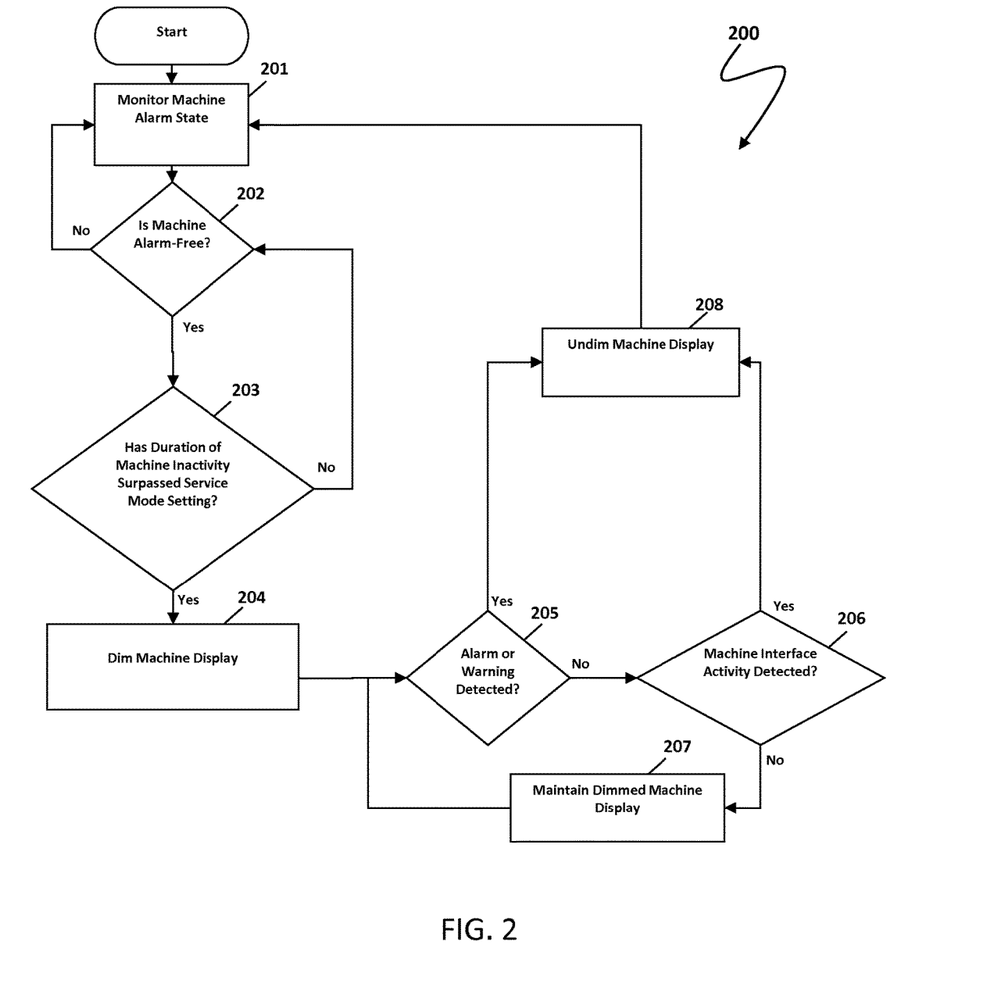
FIG. 2 is a flow diagram showing process of a control unit for placing the machine display into and out of a dimmed state in accordance with an embodiment of the system described herein.

FIG. 2 is a flow diagram 200 showing processing in connection with specific monitoring and dimness control actions taken by a control unit, like the control unit 140, according to an embodiment of the system described herein. At step 201, the machine alarm state is monitored. The process then proceeds to a decision step 202, where the machine alarm state is analyzed to determine whether an alarm-free condition is achieved before proceeding.

If the machine is experiencing an alarm state and is thereby not in an alarm-free condition (No—at step 202), then the process proceeds back to the step 201. Upon detection of an alarm-free condition (Yes—at step 202), the process proceeds to a decision step 203, where the duration of machine inactivity is analyzed to determine whether the duration of machine inactivity surpasses an amount of time set in service mode before proceeding. If not (No—at step 203), then the process goes back to the step 202, otherwise, if so (Yes—at step 203), the process proceeds to a step 204 where the display enters a dimmed state.

After the step 204, the process proceeds to a decision step 205, where the machine alarm state is analyzed to ensure that an alarm-free condition is maintained. In the event of an alarm or warning (Yes—at step 205), the proceed proceeds to step 208 where the machine display exits the dimmed state to convey alarm or warning information to the operator and the process then returns to the step 201. If an alarm or warning is not detected (No—at step 205), the machine display remains dimmed and proceeds to a decision step 206 where machine interface activity is analyzed. If machine interface activity is detected (Yes—at step 206) the process proceeds to step 208 where the machine display exits the dimmed state and the process then returns to the step 201.

If machine interface activity is not detected (No—at step 206) the process proceeds to step 207 where the dimmed state of the machine display is maintained, and the process then returns to the step 205. The process may continue through steps 205, 206, and 207 until either an alarm or warning is detected or machine interface activity is detected.

Figure 3:
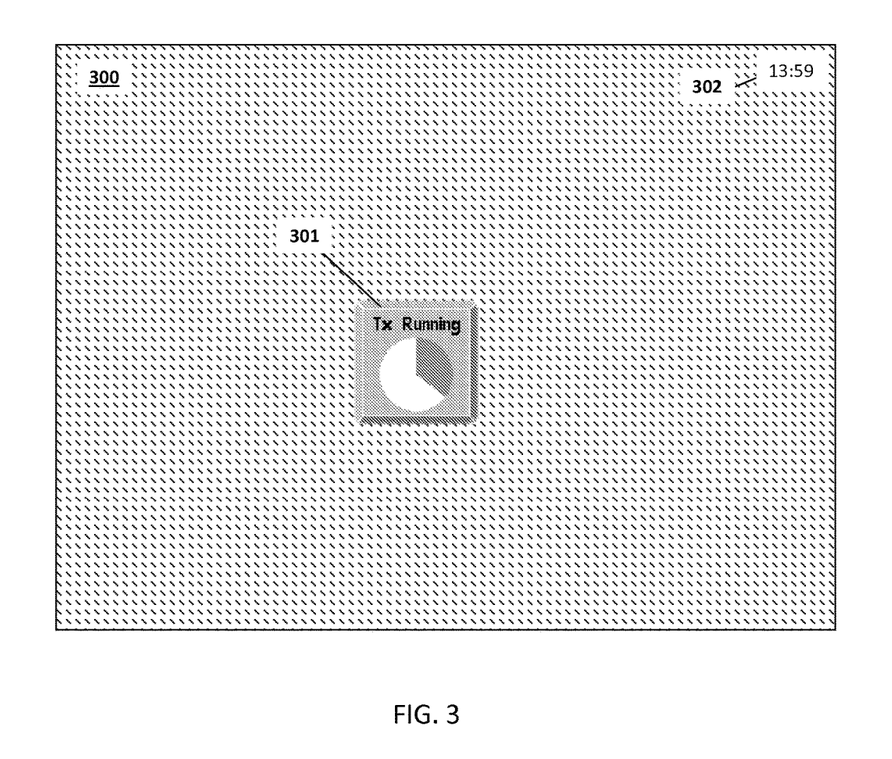
FIG. 3 is a schematic illustration of the machine display in a dimmed state in accordance with an embodiment of the system described herein.

FIG. 3 is a schematic illustration showing the display 300 in a dimmed state in accordance with an embodiment of the system described herein. The display is dimmed except for a treatment clock 301 and a clock time 302 that are illuminated. In the illustrated embodiment, as the therapy progresses, the pie-chart of the treatment clock 301 gradually fills to illustrate an approximate amount of therapy time remaining. The clock time 302 increments as the therapy progresses.

Figure 4:
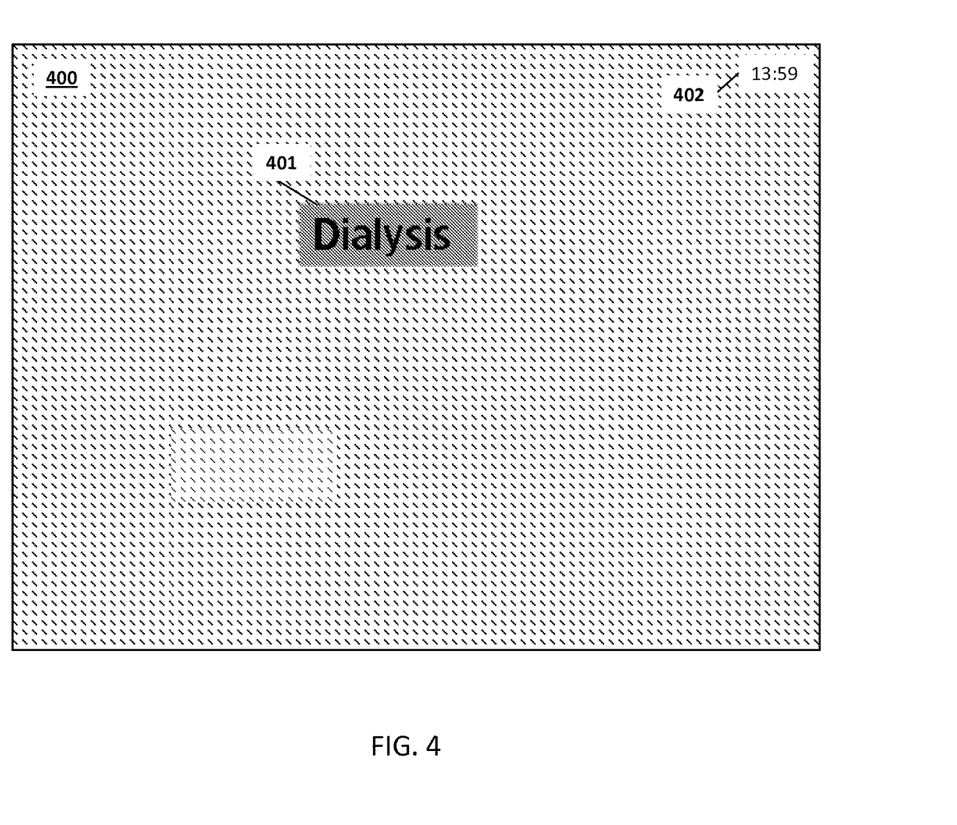
FIG. 4 is a schematic illustration of the machine display in a dimmed state in accordance with an embodiment of the system described herein.

FIG. 4 is a schematic illustration showing a display 400 in a dimmed state in accordance with an embodiment of the system described herein. The display 400 is dimmed except for a treatment status bar 401 and a clock time 402 that are illuminated. As the therapy progresses, the treatment status bar 401 displays machine state and informs the operator of the initiation of background processes such as Online Clearance Tests. The clock time 402 increments as the therapy progresses.

Figure 5:
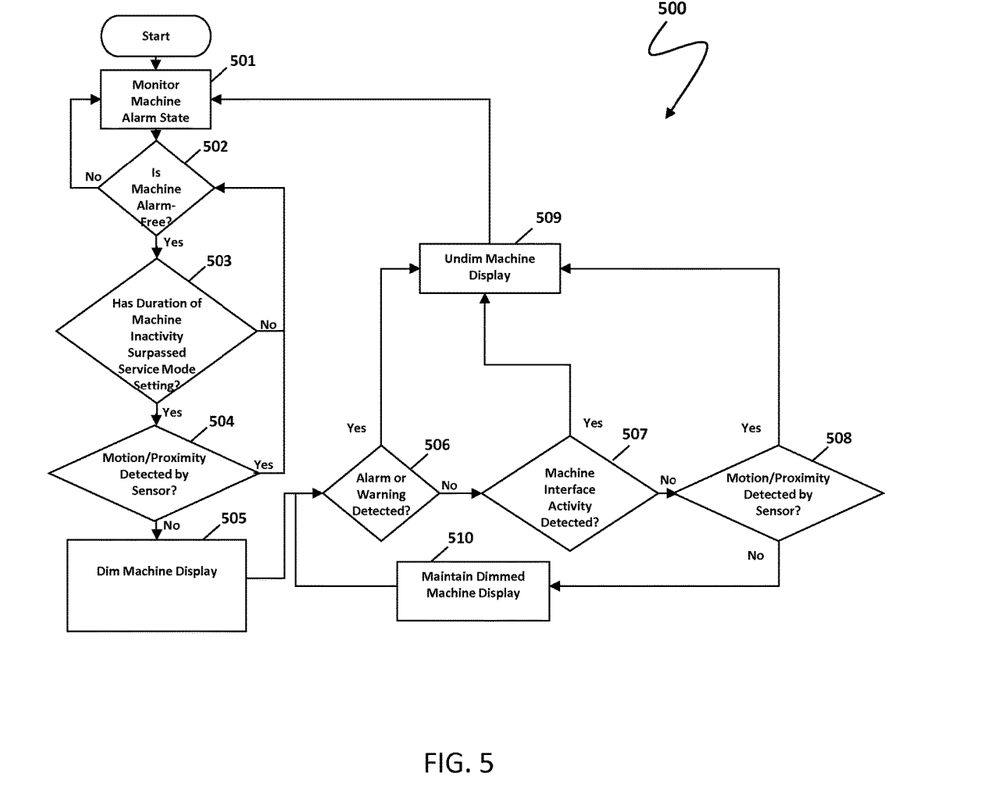
FIG. 5 is a flow diagram showing processing of a control unit for placing the machine display into and out of a dimmed state in accordance with an embodiment of the system described herein.

FIG. 5 is a flow diagram 500 showing processing in connection with specific monitoring and control actions taken by a control unit according to an embodiment of the system described herein. At step 501, the machine alarm state is monitored. The process then proceeds to a decision step 502, where the machine alarm state is analyzed to ensure that an alarm-free condition is achieved before proceeding. If an alarm is detected, meaning the system is not in an alarm-free condition (No—at step 502), then the system maintains an undimmed state and the process proceeds back to the step 501.

Upon detection of an alarm-free condition (Yes—at step 502), the process proceeds to a decision step 503, where the duration of machine interface inactivity is analyzed to determine whether the duration of machine interface inactivity surpasses an amount of time period set in service mode before proceeding. If not (No—at step 503), then processing proceeds back to the step 502. Otherwise, if the duration of machine interface inactivity has surpassed a set time period (Yes—at step 503), then the process proceeds to a decision step 504. At the decision step 504, motion or proximity detection by a motion and/or proximity sensor is analyzed to determine whether motion or proximity of a user has detected, for example, over a time period. If so (Yes—at step 504), then the process goes back to the step 502, otherwise, if no motion/proximity has been detected (No—at step 504), then the process proceeds to a step 505 where the machine display enters a dimmed state. As described herein, it is noted that the system may continuously monitor machine alarm state, along with machine interface activity and the motion/proximity detected by the motion/proximity sensor in connection with the operations of the display dimness control. It is also noted that the time periods discussed herein in connection with assessing machine alarm state, machine interface activity and/or motion/proximity detection may be adjustable and may be set independently of one another.

After the step 505, the process proceeds to a decision step 506, where the machine alarm state is analyzed to determine whether an alarm-free condition is maintained. In the event of an alarm or warning (Yes—a step 506), the proceed proceeds to step 509 where the machine display exits the dimmed state to convey alarm or warning information to the operator and the process then returns to step 501. If an alarm or warning is not detected (No—at step 506), the machine display remains dimmed and proceeds to a decision step 507 where machine interface activity is analyzed. If machine interface activity is detected (Yes—at step 507) the process proceeds to step 509 where the machine display exits the dimmed state and the process then returns to step 501.

If no machine interface activity is detected (No—at step 507), e.g. the machine interface is inactive for a set time period, then the process proceeds to a decision step 508, where motion information from the motion/proximity sensor is analyzed to determine whether motion and/or proximity has been detected by one or more sensors. In the event of movement/proximity has been detected by the motion and/or proximity detector sensor (Yes—at step 508), the process proceeds to step 509 where the machine display exits the dimmed state and the process then returns to the step 501.

If movement or proximity has not been detected by the sensor, for example, over a time period (No—at step 508), the process proceeds to step 510 where the dimmed state of the machine display is maintained, and the process then returns to the step 506. The process may continue to proceed through steps 506, 507, 508, and 510 until an alarm or warning is detected, machine interface activity is detected, or motion/proximity is detected by the motion/proximity sensor.

In other implementations, it is noted that the system described herein may be used in connection with other features involving automated and/or non-contact operations of a medical device. For example, the system described herein may be used in connection with gesture-based, hands-free interfacing between a user and the medical device (e.g. dialysis machine) and in which a controller, such as the controller 140, and sensors, such as the proximity sensor 151 and/or motion sensor 152, are also configured for operation and functions according to gesture-based control of the medical device. Accordingly, for example, recognition of user gestures at the medical device may correspond to conditions in which machine interface activity is detected (see, e.g. step 507 of FIG. 5) and/or when motion/proximity is detected by a sensor (see, e.g. step 508 of FIG. 5). For a discussion of features of non-contact, gesture-based control systems for dialysis machines and/or other medical devices, reference is made to US 2015/0253860 A1 to Merics et al., US 2014/0266983 A1 to Christensen and/or US 2014/0267003 A1 to Wang et al., which are all incorporated herein by reference.

Various embodiments discussed herein may be combined with each other in appropriate combinations in connection with the system described herein. Additionally, in some instances, the order of steps in the flow diagrams, flowcharts and/or described flow processing may be modified, where appropriate. Further, various aspects of the system described herein may be implemented or controlled using software, hardware, a combination of software and hardware and/or other computer-implemented or computer-controlled modules or devices having described features and performing described functions. The system may further include a display and/or other computer components for providing a suitable interface with a user and/or with other computers.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A medical system, comprising:
   a medical device comprising:
   a display, and
   a machine interface that receives non-contact gesture-based input from a user used to control operations and functions of the medical device; and
   a display dimness control device for controlling a dimness of the display, wherein the display dimness control device includes:
      at least one sensor that includes at least one motion sensor, wherein the at least one sensor detects at least one non-contact motion of the user in a vicinity of the display dimness control device; and
      a control unit coupled to the medical device and the at least one sensor, the control unit configured to control the dimness of the display based on a state of the medical device determined from an input received from the machine interface and based on an input received from the at least one sensor, the control unit configured to control distinct portions of the display, during a dimmed state of the display, such that at least a portion of the display remains undimmed during the dimmed state of the display,
   wherein processing of the non-contact gesture-based input received at the machine interface corresponds to:
      (i) detection of the at least one non-contact-motion by the at least one sensor that is used by the control unit to automatically control dimness of the display, and
      (ii) detection of user activity input used to control operations and functions of the medical device, and
   wherein the control unit causes the display to automatically enter the dimmed state when:
      the medical device is in an alarm-free condition for a first time period,
      no activity occurs on the machine interface of the medical device for a second time period, and
      no movement is detected in a vicinity of the medical device by the at least one sensor for a third time period.

2. The medical system according to claim 1, wherein the state of the medical device includes an alarm-free condition of the medical device.

3. The medical system according to claim 1, wherein the state of the medical device includes a condition of gesture-based interaction with the machine interface of the medical device.

4. The medical system according to claim 1, wherein the medical device is a peritoneal dialysis machine.

5. The medical system according to claim 1, wherein the medical device is a hemodialysis machine.

6. The medical system according to claim 1, wherein the control unit also controls operations of the medical device.

7. The medical system according to claim 1, wherein the first time period, the second time period, and the third time period are independent of each other.

8. The medical system according to claim 1, wherein the control unit causes the display to automatically exit the dimmed state according to at least one of the following: (i) when an alarm occurs on the medical device, (ii) when user activity occurs on the machine interface, and/or (iii) when movement is detected by the at least one sensor in the vicinity of the medical device.

9. The medical system according to claim 1, wherein, during the dimmed state of the display, the portion of the display that remains undimmed comprises a clock on the display.

10. The medical system according to claim 9, wherein the clock is a therapy clock showing a duration of a therapy performed by the medical device.

11. The medical system according to claim 1, wherein, during the dimmed state of the display, the control unit controls presentation of treatment status information on the display.

12. A method for automated dimness control of a medical device, comprising:
   monitoring for movement in proximity of the medical device using at least one sensor, wherein the at least one sensor detects at least non-contact motion of a user in a vicinity of the medical device;
   monitoring for an alarm on the medical device;
   monitoring for activity on a machine interface of the medical device, wherein the machine interface receives non-contact gesture-based input from a user used to control operations and functions of the medical device; and
   automatically causing a display of the medical device to enter a dimmed state when:
      the medical device is in an alarm-free condition for a first time period,
      no activity on the machine interface occurs for a second time period, and
      no movement is detected in a vicinity of the medical device by the at least one sensor for a third time period, wherein in the dimmed state, at least a portion of the display remains undimmed.

13. The method according to claim 12, further comprising:
   causing the display to automatically exit the dimmed state according to at least one of the following: (i) when an alarm occurs on the medical device, (ii) when user activity occurs on the machine interface, and/or (iii) when movement is detected by the at least one sensor in the vicinity of the medical device.

14. The method according to claim 12, wherein the medical device is a peritoneal dialysis machine.

15. The method according to claim 12, wherein the dialysis machine is a hemodialysis machine.

16. The method according to claim 12, wherein the first time period, the second time period, and the third time period are independent of each other.

17. The method according 12, wherein, during the dimmed state of the display, a clock is presented on the display.

18. The medical system according to claim 17, wherein the clock is a therapy clock showing a duration of a therapy performed by the medical device.

19. The method according to claim 12, wherein, during the dimmed state of the display, treatment status information is presented on the display.

20. A non-transitory computer-readable medium storing software for automated dimness control of a medical device, the software comprising:
   executable code that controls monitoring for movement in proximity of the medical device using at least one sensor, wherein the at least one sensor detects non-contact motion of a user in a vicinity of the medical device;
   executable code that controls monitoring for an alarm on the medical device;
   executable code that controls monitoring for activity on a machine interface of the medical device, wherein the machine interface receives non-contact gesture-based input from a user used to control operations and functions of the medical device;

executable code that automatically causes a display of the medical device to enter a dimmed state when:

the medical device is in an alarm-free condition for a first time period, no activity on the machine interface occurs for a second time period, and no movement is detected in a vicinity of the medical device by the at least one sensor for a third time period; and executable code that causes at least a portion of the display to remain undimmed during the dimmed state of the display.

21. The non-transitory computer-readable medium according to claim 20, wherein the software further comprises:

executable code that causes the display to automatically exit the dimmed state according to at least one of the following: (i) when an alarm occurs on the medical device, (ii) when user activity occurs on the machine interface, and/or (iii) when movement is detected by the at least one sensor in the vicinity of the medical device.

22. The non-transitory computer-readable medium according to claim 20, wherein the medical device is a dialysis machine.

23. The non-transitory computer-readable medium according to claim 20, wherein the first time period, the second time period, and the third time period are independent of each other.

24. The non-transitory computer-readable medium according to claim 20, wherein the software further comprises: executable code that, during the dimmed state of the display, presents treatment status information on the display.

* * * * *

UNITED STATES PATENT AND TRADEMARK OFFICE
CERTIFICATE OF CORRECTION

PATENT NO. : 10,332,482 B2  
APPLICATION NO. : 14/866166  
DATED : June 25, 2019  
INVENTOR(S) : Kelly Yik et al.

Page 1 of 1

It is certified that error appears in the above-identified patent and that said Letters Patent is hereby corrected as shown below:

In the Claims

Claim 17  
Column 10, Line 46, after "according" insert --to claim--.

Claim 18  
Column 10, Line 49, delete "medical system" and insert --method--.

Signed and Sealed this  
Twenty-seventh Day of August, 2019

Andrei Iancu  
*Director of the United States Patent and Trademark Office*